United States Patent
Shimogami et al.

(10) Patent No.: US 10,617,855 B2
(45) Date of Patent: *Apr. 14, 2020

(54) BALLOON CATHETER

(71) Applicant: ASAHI INTECC CO., LTD., Seto-shi, Aichi (JP)

(72) Inventors: Manabu Shimogami, Seto (JP); Takeharu Katsurada, Seto (JP)

(73) Assignee: ASAHI INTECC CO., LTD., Seto-shi (JP)

(*) Notice: Subject to any disclaimer, the term of this patent is extended or adjusted under 35 U.S.C. 154(b) by 156 days.

This patent is subject to a terminal disclaimer.

(21) Appl. No.: 15/897,459

(22) Filed: Feb. 15, 2018

(65) Prior Publication Data

US 2018/0169390 A1 Jun. 21, 2018

Related U.S. Application Data

(63) Continuation of application No. 14/304,206, filed on Jun. 13, 2014, now Pat. No. 9,931,491.

(30) Foreign Application Priority Data

Sep. 24, 2013 (JP) ................................. 2013-196792

(51) Int. Cl.
*A61M 25/10* (2013.01)
*A61M 25/00* (2006.01)
*A61M 25/01* (2006.01)

(52) U.S. Cl.
CPC ...... *A61M 25/104* (2013.01); *A61M 25/0052* (2013.01); *A61M 25/1006* (2013.01);
(Continued)

(58) Field of Classification Search
CPC ............ A61M 25/005; A61M 25/0052; A61M 25/10; A61M 25/104; A61M 25/1006; A61M 2025/1075; A61M 2025/0063
See application file for complete search history.

(56) References Cited

U.S. PATENT DOCUMENTS 5,217,482 A * 6/1993 Keith ................ A61M 25/0662
604/102.02
5,389,087 A 2/1995 Miraki
(Continued)

FOREIGN PATENT DOCUMENTS

CN 101001659 A 7/2007
EP 1 787 673 A1 5/2007
(Continued)

OTHER PUBLICATIONS

Oct. 27, 2015 Office Action issued in Japanese Application No. 2013-196792.
(Continued)

*Primary Examiner* — Katherine M Rodjom
(74) *Attorney, Agent, or Firm* — Oliff PLC

(57) ABSTRACT

A balloon catheter includes a balloon, an inner shaft, an outer shaft, and a reinforcing member that includes a protruded part that contacts with an inner surface of the outer shaft and an outer surface of the inner shaft. A pushing force of an operator can be evenly transmitted to the outer shaft and the inner shaft from the distal end of the reinforcing member, reducing a relative displacement of the outer shaft and the inner shaft.

16 Claims, 6 Drawing Sheets

(52) U.S. Cl.
CPC ............ *A61M 2025/0183* (2013.01); *A61M 2025/1075* (2013.01); *A61M 2025/1084* (2013.01)

(56) References Cited

U.S. PATENT DOCUMENTS

| | | | |
|---|---|---|---|
| 5,545,134 | A | 8/1996 | Hilaire et al. |
| 6,190,358 | B1 | 2/2001 | Fitzmaurice et al. |
| 7,794,448 | B2 | 9/2010 | Grandt et al. |
| 8,088,121 | B2 | 1/2012 | Nishide et al. |
| 8,585,612 | B2 | 11/2013 | Nishigishi |
| 8,864,705 | B2 | 10/2014 | Nishigishi |
| 2007/0060910 | A1 | 3/2007 | Grandt et al. |
| 2007/0083188 | A1* | 4/2007 | Grandt ............... A61M 25/10 604/524 |
| 2009/0247945 | A1* | 10/2009 | Levit ............... A61M 25/1002 604/103 |
| 2012/0245521 | A1* | 9/2012 | Gulachenski ..... A61M 25/0045 604/103.09 |

FOREIGN PATENT DOCUMENTS

| | | |
|---|---|---|
| EP | 2 495 006 A1 | 9/2012 |
| EP | 2 361 652 B1 | 1/2014 |
| JP | 2002-126085 A | 5/2002 |
| JP | 2011-167387 A | 9/2011 |
| JP | 2012-183127 A | 9/2012 |
| JP | 2013-106798 A | 6/2013 |

OTHER PUBLICATIONS

Mar. 12, 2015 Search Report issued in European Application No. 14169032.1.
Jan. 12, 2017 Office Action issued in U.S. Appl. No. 14/304,206.
Mar. 29, 2017 Office Action issued in Chinese Patent Application No. 201410289226.8.
Jul. 6, 2017 Office Action issued in U.S. Appl. No. 14/304,206.
Aug. 28, 2017 Office Action issued in Chinese Patent Application No. 201410289226.8.
Nov. 30, 2017 Office Action issued in Chinese Patent Application No. 201410289226.8.
U.S. Appl. No. 14/304,206, filed Jun. 13, 2014 in the name of Shimogami et al.
Apr. 9, 2018 Office Action issued in Chinese Patent Application No. 201410289226.8.
Feb. 1, 2019 Office Action issued in Chinese Patent Application No. 201410289226.8.

* cited by examiner

BALLOON CATHETER

CROSS-REFERENCE TO RELATED APPLICATIONS

This is a Continuation of application Ser. No. 14/304,206 filed Jun. 13, 2014, which claims priority to Japanese Application No. 2013-196792 filed Sep. 24, 2013. The disclosure of the prior applications is hereby incorporated by reference herein in its entirety.

BACKGROUND

The disclosed embodiments relate to a medical device. Specifically, the disclosed embodiments relate to a balloon catheter inserted into a narrow part formed in a blood vessel such that the catheter enlarges the narrow part to obtain a blood flow.

Conventionally, balloon catheters are known as therapeutic catheters that are inserted into constrictions formed in blood vessels and are enlarged therein. A balloon catheter mainly includes a balloon acting as an inflating body, an outer shaft adhered to the proximal end of the balloon, and an inner shaft inserted into the balloon and the outer shaft. The inner shaft is used for inserting a guide wire. An inflation lumen provided between the outer shaft and the inner shaft is used for passing a liquid (e.g., a contrast medium and a physiological saline) for inflating the balloon.

Known balloon catheters include an over-the-wire balloon catheter (OTW balloon catheter) having an inner shaft extending from the proximal end to the distal end to insert a guide wire, and a rapid-exchange balloon catheter (RX balloon catheter) having a guide wire port for inserting a guide wire around an intermediate part between the proximal end and the distal end and an inner shaft extending from the guide wire port to the distal end.

An RX balloon catheter features a guide wire that can be more easily replaced with another than that of an OTW balloon catheter, but the catheter has low stiffness and low pushability in a blood vessel because the guide wire is not inserted to the proximal end behind the guide wire port. In order to solve the problem, in an RX balloon catheter, a metallic reinforcing member is generally provided from the proximal end to the vicinity of the guide wire port in an inflation lumen provided between an outer shaft and an inner shaft, thereby achieving higher pushability (For example, see U.S. Pat. No. 5,389,087 and Japanese Patent Laid-Open No. 2013-106798).

In balloon catheters described above, however, the distal end of a reinforcing member is fixed to only one of the inner surface of an outer shaft and the outer surface of an inner shaft. Thus, when an operator pushes the balloon catheter to the end of the catheter, a pushing force is transmitted to only one of the outer shaft and the inner shaft through the distal end of the reinforcing member, which may displace the outer shaft and the inner shaft relative to each other. This causes the balloon catheter to have low pushability. Further, when the operator pushes the balloon catheter forward so as to insert the balloon catheter into a narrow part in a blood vessel, the distal end of the reinforcing member may detach from the inner surface of the outer shaft or the outer surface of the inner shaft, preventing transmission of a pushing force to the outer shaft or the inner shaft.

SUMMARY

The disclosed embodiments have been devised in view of the circumstances. An object of the present invention is to provide a balloon catheter that can evenly transmit a pushing force applied to a reinforcing member, to an outer shaft and an inner shaft by fixing the distal end of the reinforcing member to an adhesion part of the outer shaft and the inner shaft.

A first aspect of the present invention is a balloon catheter including: a balloon; an outer shaft adhered to a proximal end of the balloon; an inner shaft that is inserted into the outer shaft and that is adhered to a distal end of the balloon; and a reinforcing member inserted between the outer shaft and the inner shaft, wherein the reinforcing member has a distal end that is fixed by an adhesion part of the outer shaft and the inner shaft.

A second aspect of the present invention is the balloon catheter described in the first aspect, wherein the adhesion part is laterally provided with respect to the distal end of the reinforcing member in cross section.

A third aspect of the present invention is the balloon catheter described in the first or second aspect, wherein the reinforcing member has a protruded part between the distal end and the proximal end of the reinforcing member, and the protruded part is in contact with the inner surface of the outer shaft and the outer surface of the inner shaft.

A fourth aspect of the present invention is the balloon catheter described in one of the first to third aspects, wherein the reinforcing member is a hollow coil member formed by twisting a plurality of wires.

In the balloon catheter according to the first aspect of the present invention, the distal end of the reinforcing member is fixed by the adhesion part of the outer shaft and the inner shaft. Thus, when an operator pushes the balloon catheter toward the distal end of the balloon catheter, a pushing force is evenly transmitted to the outer shaft and the inner shaft from the reinforcing member through the adhesion part, reducing a relative displacement of the outer shaft and the inner shaft. Moreover, even when the balloon catheter is pushed strongly toward a narrow part, the distal end of the reinforcing member is fixed by the adhesion part and thus reduces the potential of detachment of the distal end of the reinforcing member from the inner surface of the outer shaft or the outer surface of the inner shaft.

In the balloon catheter according to the second aspect of the present invention, the adhesion part is laterally provided with respect to the distal end of the reinforcing member in cross section. Thus, even if the reinforcing member has a large outside diameter, the distal end of the reinforcing member can be fixed by the laterally provided adhesion part. This can more reliably transmit a pushing force of the operator toward the distal end of the reinforcing member and reduce bending of the distal end of the reinforcing member when the operator strongly pushes the balloon catheter.

In the balloon catheter according to the third aspect of the present invention, the reinforcing member has a protruded part between the distal end and the proximal end of the reinforcing member, and the protruded part is in contact with the inner surface of the outer shaft and the outer surface of the inner shaft. The outside diameter of the protruded part provided on the reinforcing member is nearly equal to a difference obtained by subtracting the outside diameter of the inner shaft from the inside diameter of the outer shaft. Thus, the inner shaft is pushed to the inner surface of the outer shaft by the protruded part so as to fix the outer shaft and the inner shaft. With this configuration, even if the operator strongly pushes the balloon catheter toward the distal end of the catheter so as to detach the distal end of the reinforcing member from the adhesion part, the outer shaft and the inner shaft are fixed by the protruded part. Thus, a pushing force is evenly transmitted to the outer shaft and the inner shaft through the protruded part, and a relative displacement of the outer shaft and the inner shaft may still be reduced.

In the balloon catheter according to the fourth aspect of the present invention, the reinforcing member is a hollow coil member formed by twisting a plurality of wires. Thus, the hollow part of the reinforcing member is usable as a path of a liquid (e.g., a contrast medium and a physiological saline), thereby shortening the inflation or deflation time of the balloon. Further, the reinforcing member is formed by the coil member and thus the coil member rotates with the balloon catheter when rotated by an operator. This can transmit the turning force of the operator to the distal end of the balloon catheter through the distal end of the coil member.

DETAILED DESCRIPTION OF EMBODIMENTS

Figure 1:
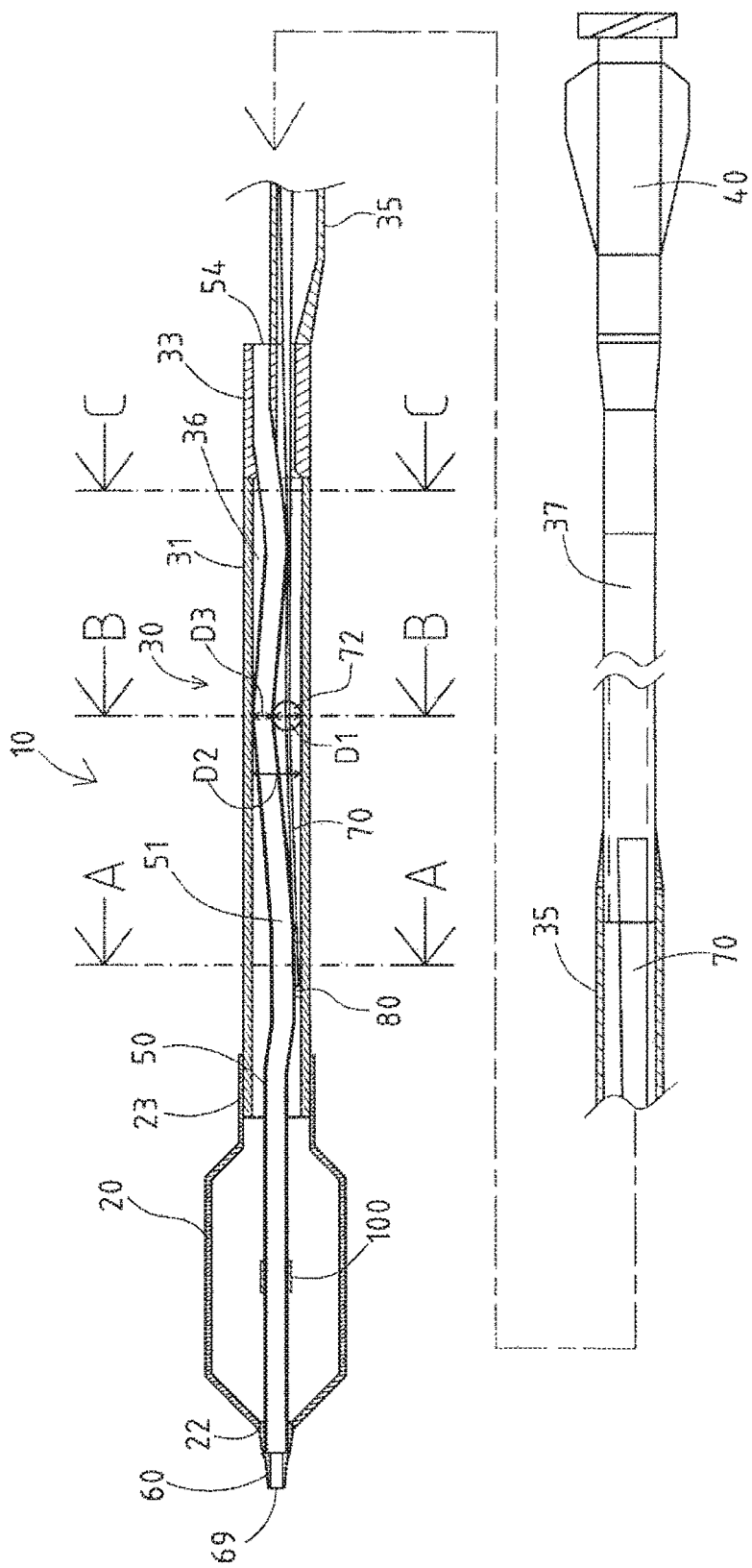
FIG. 1 is an overall view of a balloon catheter according to one embodiment.
Figure 2C:
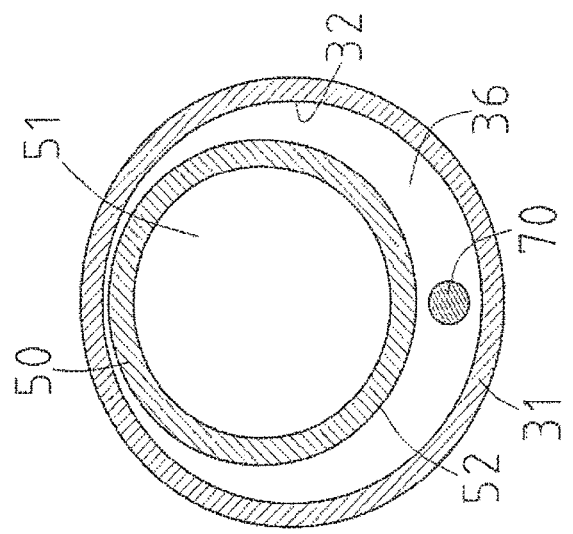
FIG. 2C is a cross-sectional view taken along line C-C of FIG. 1.

Referring to FIGS. 1 to 2C, a balloon catheter 10 according to the one embodiment will be described in the following example. In FIG. 1, the left side indicates a distal end to be inserted into a body while the right side indicates a proximal end operated by an operator, e.g., a doctor.

For example, the balloon catheter 10 is used for treating a narrow part formed in a heart vessel. As shown in FIG. 1, the balloon catheter 10 mainly includes a balloon 20, an outer shaft 30, a connector 40, an inner shaft 50, a tip 60, and a reinforcing member 70.

The balloon 20 for enlarging a narrow part is a resin member including a distal-end attachment part 22 on the distal end and a proximal-end attachment part 23 on the proximal end. The distal-end attachment part 22 adheres to the distal end of the inner shaft 50 and the tip 60 while the proximal-end attachment part 23 adheres to the distal end of the outer shaft 30. In FIG. 1, the distal-end attachment part 22 adheres to the distal end of the inner shaft 50 via the tip 60. The present embodiment is not limited to this configuration. For example, the distal-end attachment part 22 may be held between the distal end of the inner shaft 50 and the tip 60. In FIG. 1, the proximal-end attachment part 23 adheres to the outer surface of the distal end of the outer shaft 30. The present embodiment is not limited to this configuration. For example, the proximal-end attachment part 23 may be adhered to the inner surface of the distal end of the outer shaft 30.

The outer shaft 30 is a cylindrical member constituting an inflation lumen 36 for supplying a liquid such as a contrast medium and a physiological saline to inflate the balloon 20. The outer shaft 30 includes, from the distal end, a distal-end outer shaft 31, a guide wire port 33, an intermediate outer shaft 35, and a proximal-end outer shaft 37. The distal-end outer shaft 31 and the intermediate outer shaft 35 are tubes made of resins such as polyamide, polyamide elastomer, polyolefin, polyester, and polyester elastomer. The guide wire port 33 is a joining part of the distal-end outer shaft 31, the intermediate outer shaft 35, and the inner shaft 50.

The inner shaft 50 is inserted into the distal-end outer shaft 31. The inflation lumen 36 is formed between the distal-end outer shaft 31 and the inner shaft 50.

The proximal-end outer shaft 37 is a metallic cylindrical member that is called a hypotube. The distal end of the proximal-end outer shaft 37 is inserted into the proximal end of the intermediate outer shaft 35 and is adhered therein. The connector 40 is attached to the proximal end of the proximal-end outer shaft 37. When a liquid such as a contrast medium and a physiological saline is supplied to inflate the balloon 20 from an indeflator (not shown) attachable to the connector 40, the liquid passes through the inflation lumen 36 and inflates the balloon 20. The material of the proximal-end outer shaft 37 is not particularly limited. The proximal-end outer shaft 37 may be made of a superelastic alloy such as stainless steel (SUS304) and a Ni—Ti alloy.

The inner shaft 50 forms a guide wire lumen 51 in which a guide wire is inserted. The proximal end of the inner shaft 50 adheres to the guide wire port 33 of the outer shaft 30 to form a proximal-end guide wire port 54.

The distal end of the inner shaft 50 adheres to the tip 60 and the distal-end attachment part 22 of the balloon 20. The tip 60 is a soft resin member having a tapered outside shape that gradually decreases in outside diameter toward the distal end of the tip 60. A resin that forms the tip 60 is not particularly limited. For example, polyurethane and polyurethane elastomer may be used.

The tip 60 is a cylindrical member adhered to the distal end of the guide wire lumen 51. A distal-end guide wire port 69 is provided on the distal end of the tip 60.

The inner shaft 50 includes a radiopaque marker 100 that is attached in the balloon 20 to locate the balloon 20 under radiation exposure.

The reinforcing member 70 is attached to the inner surface of the distal end of the distal-end outer shaft 37. The reinforcing member 70 is circular in cross section and is a tapered metallic wire rod that decreases in diameter toward the distal end of the reinforcing member 70. The material of the reinforcing member 70 is not particularly limited. The reinforcing member 70 may be made of a superelastic alloy such as stainless steel (SUS304) and a Ni—Ti alloy.

The reinforcing member 70 passes through the intermediate outer shaft 35 and the guide wire port 33 and then extends to the distal-end outer shaft 31.

Figure 2B:
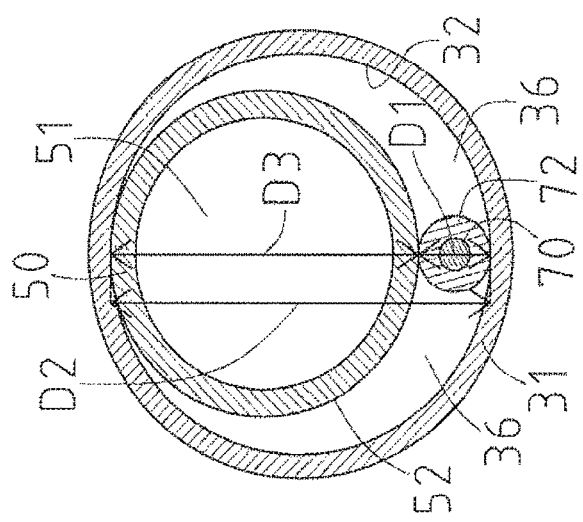
FIG. 2B is a cross-sectional view taken along line B-B of FIG. 1.
Figure 2A:
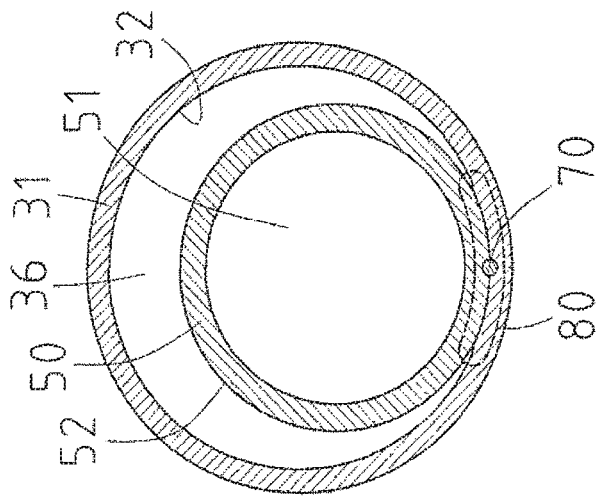
FIG. 2A is a cross-sectional view taken along line A-A of FIG. 1.

The distal end of the reinforcing member 70 is fixed by an adhesion part 80 of the distal-end outer shaft 31 and the inner shaft 50 (see FIGS. 1 and 2A). Since the inner shaft 50 is made of resin like the distal-end outer shaft, the adhesion part 80 can be formed by adhering the distal-end outer shaft 31 and the inner shaft 50 by laser and so on.

Since the distal end of the reinforcing member 70 is fixed by the adhesion part 80, when an operator pushes the balloon catheter 10 toward the distal end of the catheter, a pushing force is evenly transmitted to the distal-end outer shaft 31 and the inner shaft 50 through the adhesion part 80 from the distal end of the reinforcing member 70. This reduces a relative displacement of the distal-end outer shaft 31 and the inner shaft 50. Since the distal end of the reinforcing member 70 is fixed by the adhesion part 80, the distal end of the reinforcing member 70 is less likely to be removed from an inner surface 32 of the distal-end outer shaft 31 or an outer surface 52 of the inner shaft 50 when the balloon catheter 10 pressed into a narrow part.

Figure 3:
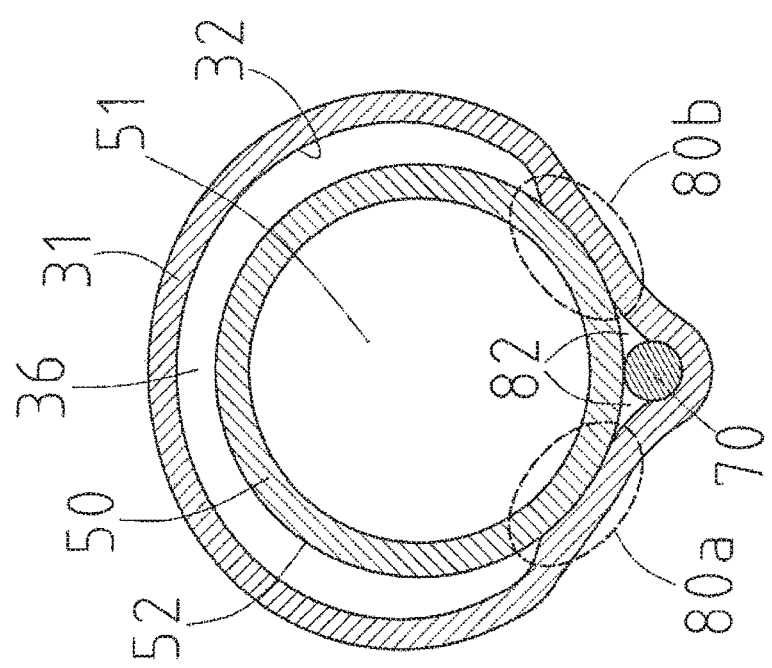
FIG. 3 shows a modification of FIG. 2A, in which adhesion parts are symmetrically formed with respect to the distal end of a reinforcing member.

In FIG. 2A, the narrow distal end of the reinforcing member 70 is embedded and fixed into the adhesion part 80 formed by the inner surface 32 of the distal-end outer shaft 31 and the outer surface 52 of the inner shaft 50. The present embodiment is not limited to this configuration. For example, if the reinforcing member 70 has a large outside diameter as shown in FIG. 3, an adhesion part 80a and an adhesion part 80b may be laterally provided in cross section with respect to the distal end of the reinforcing member 70. The reinforcing member 70 having a large outside diameter makes it possible to more reliably transmit a pushing force of an operator to the distal end of the reinforcing member 70 and reduce bending of the distal end of the reinforcing member 70 when the operator strongly pushes the balloon catheter 10. At this point, a gap 82 is formed between the distal end of the reinforcing member 70 and the adhesion part 80a or between the distal end of the reinforcing member 70 and the adhesion part 80b. The gap 82 is used as a path of a liquid such as a contrast medium and a physiological saline in addition to the inflation lumen 36. Thus, even if the reinforcing member 70 has a large outside diameter, the balloon 20 can be quickly inflated or deflated.

As shown in FIG. 1, the reinforcing member 70 has a protruded part 72 between the distal end and the proximal end of the reinforcing member 70. The protruded part 72 is in contact with the inner surface 32 of the distal-end outer shaft 31 and the outer surface 52 of the inner shaft. The protruded part 72 has an outside diameter D1 that is nearly equal to a difference obtained by subtracting an outside diameter D3 of the inner shaft 50 from an inside diameter D2 of the distal-end outer shaft 31 (D1≈D2−D3) (See FIG. 2B). Thus, the outer surface 52 of the inner shaft 50 is pushed to the inner surface 32 of the distal-end outer shaft 31 by the protruded part 72 so as to fix the distal-end outer shaft 31 and the inner shaft 50. With this configuration, even if the operator strongly pushes the balloon catheter 10 to the distal end of the catheter so as to detach the distal end of the reinforcing member 70 from the adhesion part 80, the distal-end outer shaft 31 and the inner shaft 50 are fixed by the protruded part 72. Thus, a pushing force is evenly transmitted to the distal-end outer shaft 31 and the inner shaft 50 through the protruded part 72, and a relative displacement of the distal-end outer shaft 31 and the inner shaft 50 may still be reduced.

The protruded part 72 may be made of a superelastic alloy such as stainless steel (SUS304) and a Ni—Ti alloy or a radiopaque material (e.g., gold, platinum, tungsten, and an alloy of these metals). If the protruded part 72 is made of a radiopaque material, an operator can locate the protruded part 72 as well as the marker 100 under radiation exposure. If a distance between the position of the marker 100 and the position of the protruded part 72 does not remain constant during an operation of the balloon catheter 10, it is understood that the reinforcing member 70 is detached from the distal-end outer shaft 31 and the inner shaft 50 and is unfixed. Thus, an operator can identify a time to replace the balloon catheter 10 by means of the marker 100 and the protruded part 72.

As shown in FIGS. 1 and 2C, the reinforcing member 70 is mostly unfixed to the outer shaft 30 and the inner shaft 50.

As described above, in the distal-end outer shaft 31, the reinforcing member 70 is fixed to the outer shaft 30 and the inner shaft 50, at the distal end and the protruded part 72. The number of protruded parts 72 is not limited to one. The larger the number of parts fixing reinforcing members 70 to the outer shaft 30 and the inner shaft 50, the narrower the inflation lumen 36 provided between the outer shaft 30 and the inner shaft 50. This prevents quick inflation and deflation of the balloon 20. For this reason, it is not preferable to provide an excessive number of protruded parts 72.

Figure 4:
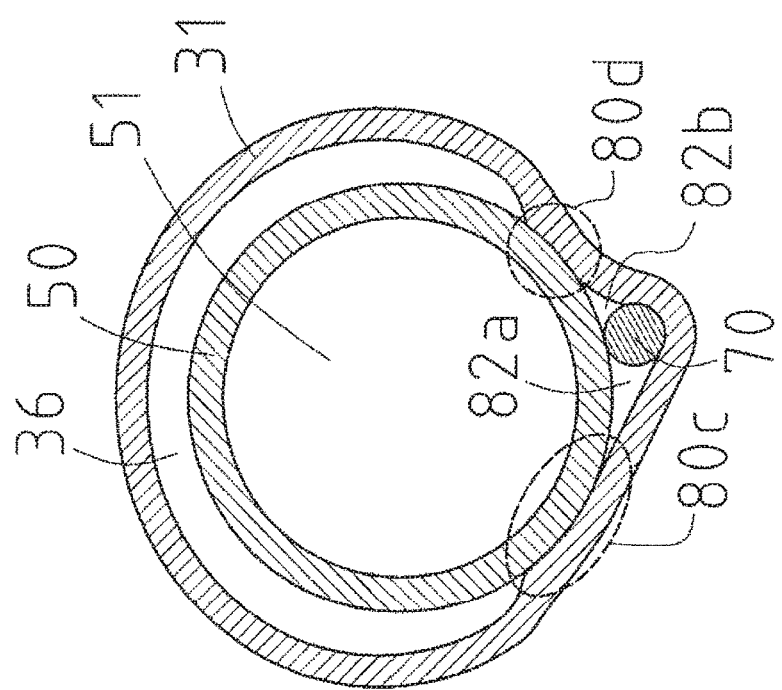
FIG. 4 shows a modification of FIG. 3, in which adhesion parts are asymmetrically formed with respect to the distal end of the reinforcing member.

In FIG. 3, the adhesion parts 80a and 80b are symmetrically formed with respect to the distal end of the reinforcing member 70. The present embodiment is not limited to this configuration. For example, as shown in FIG. 4, adhesion parts 80c and 80d may be asymmetrically formed with respect to the distal end of the reinforcing member 70 such that the adhesion part 80c is larger than the adhesion part 80d. At this point, a gap 82a is provided between the distal end of the reinforcing member 70 and the adhesion part 80c while a gap 82b is provided between the distal end of the reinforcing member 70 and the adhesion part 80d. As in FIG. 2A, the gaps 82a and 82b are used as paths of a liquid such as a contrast medium and a physiological saline in addition to the inflation lumen 36, thereby quickly inflating or deflating the balloon 20.

Figure 5:
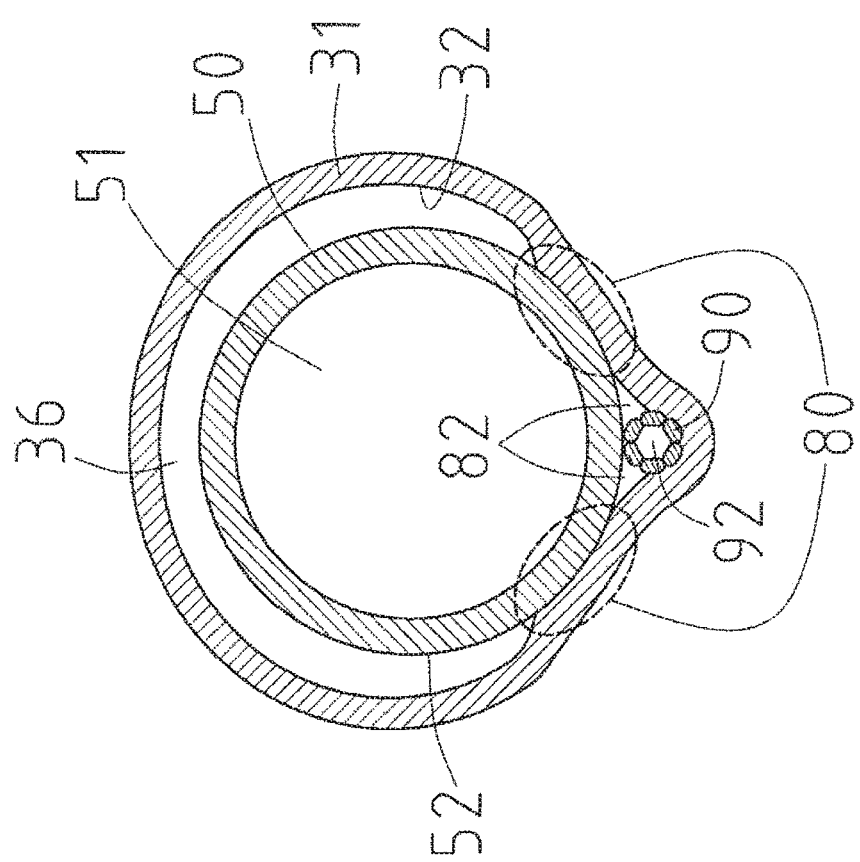
FIG. 5 shows a modification of FIG. 3, in which the reinforcing member is formed by a hollow coil member.

In the above explanation, the reinforcing member 70 is a wire rod that is circular in cross section. The present embodiment is not limited to this configuration. For example, as shown in FIG. 5, the reinforcing member may be a hollow coil member 90 formed by twisting a plurality of wires. The coil member 90 is also usable as a path of a liquid (e.g., a contrast medium and a physiological saline) in addition to the inflation lumen 36 and the gap 82, 82a, 82b, thereby shortening the inflation or deflation time of the balloon 20. The reinforcing member is formed by the coil member 90 and thus the coil member 90 rotates with the balloon catheter 10 when rotated by an operator. This can transmit the turning force of the operator to the distal end of the balloon catheter 10 through the distal end of the coil member 90 serving as a reinforcing member.

Wires constituting the coil member 90 serving as a reinforcing member may be round wires or flat wires. Flat wires are more preferable to increase the area of a hollow part 92. Alternatively, stranded wires are used as wires constituting the coil member 90 and rope coils of stranded wires (that is, strands of twisted wires) constitute the coil member 90. Thus, the turning force of an operator can be reliably transmitted to the distal end of the balloon catheter 10 through the distal end of the coil member 90 serving as a reinforcing member.

Figure 6:
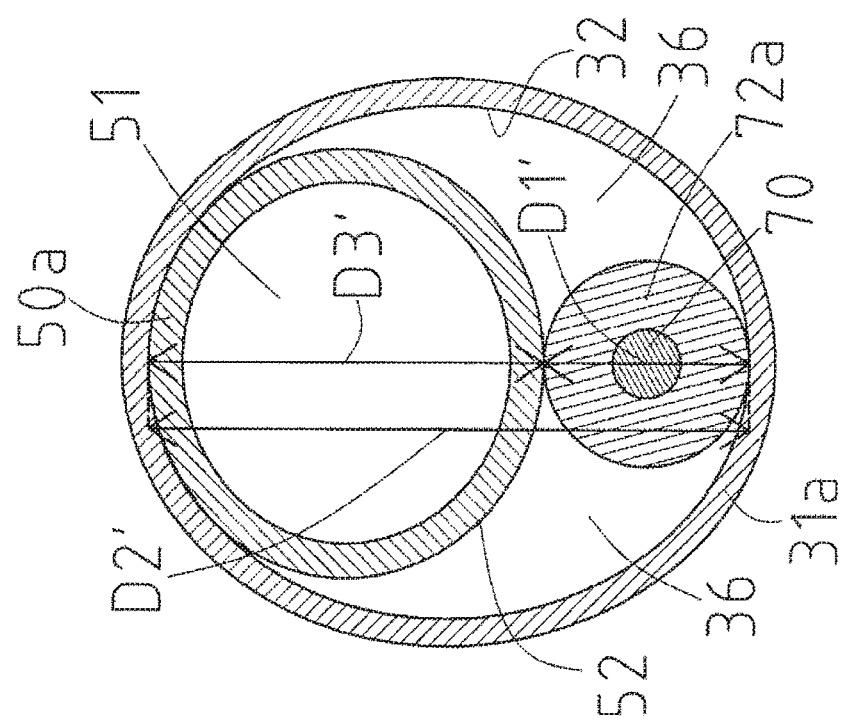
FIG. 6 shows a modification of FIG. 2B, in which a protruded part having a large outside diameter is inserted into an inflation lumen provided between an outer shaft and an inner shaft.

As shown in FIG. 6, a protruded part 72a that is larger in outside diameter than in FIG. 2B may be inserted into the inflation lumen 36 between an outer shaft 31a and an inner shaft 50a. At this point, the protruded part 72a has an outside diameter D1' that is larger than the outside diameter D1 of the protruded part 72 (D1'>D1). Thus, the inner shaft 50a is strongly pushed to the inner surface 32 of the distal-end outer shaft 31a by the protruded part 72a and forms a horizontal oval. With this configuration, the outside diameter D3' of the inner shaft 50a is smaller than the outside diameter D3 of the inner shaft 50 (D3'<D3) in cross section; meanwhile, the distal-end outer shaft 31a is shaped like a vertical oval. Hence, the distal-end outer shaft 31a has an inside diameter D2' that is larger than the inside diameter D2 of the distal-end outer shaft 31a (D2'>D2). This strongly fixes the distal-end outer shaft 31a and the inner shaft 50a. Hence, even if the distal end of the reinforcing member 70 is detached from the adhesion part 80, a pushing force of an operator is evenly transmitted toward the distal-end outer shaft 31a and the inner shaft 50a through the protruded part 72a, preventing a relative displacement of the distal-end outer shaft 31a and the inner shaft 50a.

As described above, in the balloon catheter 10, the distal end of the reinforcing member 70 is fixed by the adhesion part 80 of the outer shaft 30 and the inner shaft 50. Thus, a pushing force of an operator is evenly transmitted to the outer shaft 30 and the inner shaft 50 from the distal end of the reinforcing member 70 through the adhesion part 80, reducing a relative displacement of the outer shaft 30 and the inner shaft 50. Furthermore, the adhesion part 80 can reduce the detachment of the distal end of the reinforcing member 70 from the outer shaft 30 or the inner shaft 50.

What is claimed is:

1. A balloon catheter comprising:
   a balloon having a proximal end and a distal end;
   an outer shaft connected to the proximal end of the balloon;
   an inner shaft that is disposed within the outer shaft and the balloon, and that is connected to the distal end of the balloon; and
   a reinforcing member having a protruded part and that is disposed between the outer shaft and the inner shaft, wherein:
   the protruded part contacts with an inner surface of the outer shaft and an outer surface of the inner shaft, and
   the inner shaft is bent toward the outer shaft at a position of the protruded part as a result of contact between the inner shaft, the reinforcing member, and the outer shaft.

2. The balloon catheter according to claim 1, wherein an outer diameter of the reinforcing member varies along the length of the reinforcing member and is largest at the protruded part.

3. The balloon catheter according to claim 2, wherein the inner surface of the outer shaft or the outer surface of the inner shaft is pressed against the protruded part.

4. The balloon catheter according to claim 3, wherein a diameter of the protruded part is of a size such that, at the position of the protruded part, the outer shaft forms an oval elongated along a first direction perpendicular to an axis of the outer shaft, and the inner shaft forms an oval elongated in a second direction that is perpendicular to the first direction.

5. The balloon catheter according to claim 2, wherein a diameter of the protruded part is of a size such that, at the position of the protruded part, the outer shaft forms an oval elongated along a first direction perpendicular to an axis of the outer shaft, and the inner shaft forms an oval elongated in a second direction that is perpendicular to the first direction.

6. The balloon catheter according to claim 2, wherein the reinforcing member is a hollow coil member formed by a plurality of twisted wires.

7. The balloon catheter according to claim 6, wherein wires constituting each of the twisted wires are flat wires.

8. The balloon catheter according to claim 2, wherein the inner shaft is biased against the inner surface of the outer shaft by the protruded part so as to fix the outer shaft and the inner shaft relative to each other.

9. The balloon catheter according to claim 1, wherein the inner surface of the outer shaft or the outer surface of the inner shaft is pressed against the protruded part.

10. The balloon catheter according to claim 9, wherein a diameter of the protruded part is of a size such that, at the position of the protruded part, the outer shaft forms an oval elongated along a first direction perpendicular to an axis of the outer shaft, and the inner shaft forms an oval elongated in a second direction that is perpendicular to the first direction.

11. The balloon catheter according to claim 1, wherein a diameter of the protruded part is of a size such that, at the position of the protruded part, the outer shaft forms an oval elongated along a first direction perpendicular to an axis of the outer shaft, and the inner shaft forms an oval elongated in a second direction that is perpendicular to the first direction.

12. The balloon catheter according to claim 1, wherein the reinforcing member is a hollow coil member formed by a plurality of twisted wires.

13. The balloon catheter according to claim 12, wherein wires constituting each of the twisted wires are flat wires.

14. The balloon catheter according to claim 1, wherein the inner shaft is biased against the inner surface of the outer shaft by the protruded part so as to fix the outer shaft and the inner shaft relative to each other.

15. A balloon catheter comprising:
    a balloon having a proximal end and a distal end;
    an outer shaft connected to the proximal end of the balloon;
    an inner shaft that is disposed within the outer shaft and the balloon, and that is connected to the distal end of the balloon; and
    a reinforcing member having a protruded part and that is disposed between the outer shaft and the inner shaft, wherein the protruded part has a spherical shape and contacts with an inner surface of the outer shaft and an outer surface of the inner shaft.

16. A balloon catheter comprising:
    a balloon having a proximal end and a distal end;
    an outer shaft connected to the proximal end of the balloon;
    an inner shaft that is disposed within the outer shaft and the balloon, and that is connected to the distal end of the balloon; and
    a reinforcing member having a protruded part and that is disposed between the outer shaft and the inner shaft, wherein:
    the protruded part has a spherical shape and contacts with an inner surface of the outer shaft, and
    only one portion of the protruded part in a circumferential direction of the protruded part contacts with an outer surface of the inner shaft.

\* \* \* \* \*